(12) United States Patent
Cole et al.

(10) Patent No.: US 6,387,098 B1
(45) Date of Patent: May 14, 2002

(54) INTRAMEDULLARY CATHETER NAIL APPARATUS AND METHOD

(76) Inventors: Peter Alexander Cole, 123 Carriage La., Madison, MS (US) 39110; Douglas Eric Parsell, 327 Arlington Cir., Ridgeland, MS (US) 39157

( * ) Notice: Subject to any disclaimer, the term of this patent is extended or adjusted under 35 U.S.C. 154(b) by 0 days.

(21) Appl. No.: 09/557,786

(22) Filed: Apr. 22, 2000

Related U.S. Application Data

(60) Provisional application No. 60/160,453, filed on Oct. 21, 1999.

(51) Int. Cl.$^7$ .............................................. A61B 17/72
(52) U.S. Cl. ........................................ 606/62; 606/67
(58) Field of Search ..................... 606/62, 67

(56) References Cited

U.S. PATENT DOCUMENTS

| | | | |
|---|---|---|---|
| 3,256,877 A | * 6/1966 | Haboush | 606/67 |
| 4,218,255 A | 8/1980 | Bajpai et al. | |
| 4,347,234 A | 8/1982 | Wahlig et al. | |
| 4,441,492 A | * 4/1984 | Rydell et al. | 606/67 |
| 4,563,489 A | 1/1986 | Urist | |
| 4,653,487 A | * 3/1987 | Maale | 606/62 |
| 4,772,261 A | 9/1988 | Van Hoff | |
| 4,863,444 A | * 9/1989 | Blomer | 606/67 |
| 4,919,666 A | 4/1990 | Buchhorn et al. | |
| 4,946,929 A | 8/1990 | D'Amore et al. | |
| 4,976,714 A | 12/1990 | Aghion | |
| 5,034,013 A | 7/1991 | Kyle et al. | |
| 5,041,115 A | * 8/1991 | Frigg et al. | 606/67 |
| 5,100,404 A | 3/1992 | Hayes | |
| 5,112,333 A | 5/1992 | Fixel | |
| 5,203,770 A | 4/1993 | Wigness et al. | |
| 5,268,178 A | 12/1993 | Calhoun et al. | |
| 5,545,409 A | 8/1996 | Laurencin et al. | |
| 5,607,474 A | 3/1997 | Athanasiou et al. | |
| 5,618,286 A | * 4/1997 | Brinker | 606/62 |
| 5,629,009 A | 5/1997 | Laurencin et al. | |
| 5,658,287 A | 8/1997 | Hoffman et al. | |
| 5,681,289 A | * 10/1997 | Wilcox et al. | 606/62 |
| 5,702,446 A | 12/1997 | Schenck et al. | |
| 5,779,705 A | 7/1998 | Matthews | |
| 5,814,047 A | 9/1998 | Emilio et al. | |
| 5,836,949 A | 11/1998 | Campbell, Jr. et al. | |
| 5,849,331 A | 12/1998 | Ducheyne et al. | |
| 5,855,915 A | 1/1999 | Pinkus | |
| 5,972,384 A | 10/1999 | Thut et al. | |
| 6,033,407 A | 3/2000 | Behrens | |
| 6,077,265 A | * 6/2000 | Werding et al. | 606/67 |

* cited by examiner

*Primary Examiner*—Paul J. Hirsch
(74) *Attorney, Agent, or Firm*—Workman, Nydegger & Seeley

(57) ABSTRACT

An intramedullary catheter nail apparatus and method is disclosed that provides both the mechanical stabiliazation and therapeutic drug delivery needed to optimize long bone repair. In the preferred embodiment, the intramedullary catheter nail contains circular channels running along its length that have open communication with the outer surface of the nail, but are primarily receded within the nail. Enclosed in these channels are end-capped, catheter tubes with perforated regions mared with radiographically-visible rings. Once the nail is mechanically fixed within the repaired long bone, the catheter tubes are retracted the needed distance so as to position the perforated regions adjacent to the site of bone fracture or disease. Internal catheter tubes would preferably unite as exiting the nail. Catheter tubing would exit the patient's body through a subcutaneous port, thus allowing convenient and sterile connection to a pumping source of therapeutic agents, such as an infusion pump. The delivery of growth factors, analgesics, chemotherapeutic, antibiotics, anti-inflammatories, diagnostic agents or mixtures of various components of differing classes directly to the trauma site would be facillitated.

20 Claims, 2 Drawing Sheets

INTRAMEDULLARY CATHETER NAIL APPARATUS AND METHOD

RELATED APPLICATIONS

This application claims the benefit of Provisional Patent Application Serial No. 60/160,453, filed Oct. 21, 1999.

BACKGROUND OF THE INVENTION

1. The Field of the Invention

This invention relates to a device consisting of a modified intramedullary nail that contains the means for delivery of therapeutic and/or diagnostic agents directly to the fracture site.

2. The Relevant Technology

Intramedullary nails are used by orthopedic surgeons to stabilize long bone fractures. Bones typically involved would include femur, radius, ulna, humerus, fibula and tibia. The concept of intramedullary stabilization consists of mechanical reaming of the medullary canal, insertion of a form-fitting, rigid implant into the canal space and mechanically affixing the implant through insertion of screws or pins that travel through both the bone and the intramedullary device. Many variations of the intramedullary nail have been developed to address issues of strength, flexibility, ease of insertion and conformity to anatomical form. Some of the patented intramedullary nail apparatuses which deal with these mechanical concerns include U.S. Pat. No. 6,033,407 by Behrens, U.S. Pat. No. 5,814,047 by Emiho, U.S. Pat. No. 5,112,333 by Fixel, U.S. Pat. No. 5,100,404 by Hayes, U.S. Pat. No. 5,034,013 by Kyle, U.S. Pat. No. 4,976,714 by Aghion, U.S. Pat. No. 5,779,705 by Matthews, and U.S. Pat. No. 5,658,287 by Hofinann.

Beyond the mechanical requirements for stabilization of long bone fractures, many issues relating to the biochemistry of bone healing are of great significance for determining the outcome of medical intervention. To this end, many devices and materials have been designed to facilitate the delivery of therapeutic agents to the traumatized area. One of the earliest means for controlled introduction of therapeutic agents into a patient is through catheter delivery. Catheter delivery of agents is typically systemic due to the direct introduction of said agents into the patient's bloodstream.

Several works more directly target bones with catheter systems. U.S. Pat. No. 5,203,770 by Wigness reveals a catheter system that travels through bones for better access to internal joint surfaces. Delivery of therapeutic agents directly to a joint surface is thought to facilitate a therapy for arthritic conditions. U.S. Pat. No. 4,772,261 by Von Hoff reveals a catheter system that delivers therapeutic agents into the intramedullary canal of non-traumatic bones, via a bone tap, which then functions as a semi-continuous drug-releasing reservoir for the entire body.

An alternative method for continuous delivery of therapeutic agents involves the bioerosion of an implantable material which releases into solution a variety of therapeutic substances. Polymer and polymer/ceramic composite materials are most often utilized as the matrix material. They both show good biocompatibility and are readily eroded in a physiological environment. A significant problem with these systems is that they both lack the mechanical strength to safely stabilize long bone fractures. Polymeric matrix systems for the delivery of a host of therapeutics via bioerosion include U.S. Pat. No. 5,855,915 by Pinkus, U.S. Pat. No. 5,629,009 and U.S. Pat. No. 5,545,409 by Laurencin, U.S. Pat. No. 5,607,474 by Athanasiou, U.S. Pat. No. 5,268,178 by Calhoun, U.S. Pat. No. 4,946,929 by D'Amore, U.S. Pat. No. 4,347,234 by Wahlig and U.S. Pat. No. 4,563,489 by Urist. Examples of ceramic-based bioerosion delivery systems would include U.S. Pat. No. 5,849,331 by Ducheyne, U.S. Pat. No. 4,218,255 by Bajpai and U.S. Pat. No. 5,972,384 by Thut.

The idea of merging the needed mechanical stabilization of a metallic intramedullary nail with therapeutic drug delivery has been conceived by several inventors. U.S. Pat. No. 5,618,286 by Brinker reveals an intramedullary fixation implant that includes solid antibiotic material packed along grooves in the implant. Significant drawbacks with this design include the inability to modify drug dosage or type once inserted and the inability to specifically target the fracture site for drug delivery. This design also does not allow for mechanical stabilization to be obtained, followed by an interval of no intraosseous therapeutic intervention prior to the possible initiation of pharmacological therapy. This would be beneficial because the potential for unassisted healing could be assessed, with the option of subsequent therapeutic intervention remaining available. U.S. Pat. No. 4,919,666 by Buchhorn reveals a design very similar to U.S. Pat No. 5,618,286 with the addition of a porous covering over the bioeroding agent to prevent bone growth into the grooves of the implant. As with the previous design, drawbacks with this design include the inability to modify drug dosage, regimen or type once inserted and the inability to specifically target the fracture site for drug delivery. U.S. Pat. No. 5,702,446 by Schenek reveals a hip stem prosthesis with internal channels that allows irrigation of an endosteal bone/prosthesis mesh surface via external injection of therapeutic fluids through a connected catheter tube. While this design would allow for modification of the drug profile, the delivery of the drug is not specific to a fracture site and the device provides no mechanism for fracture fixation. U.S. Pat. No. 5,836,949 by Campbell reveals a totally bioresorbable intramedullary nail. The nail is proposed to provide stabilization during the early stages of bone repair and effectively disappear over an extended period of time therefore eliminating issues associated with post-utility implant presence. Short-comings with this design include reduced mechanical strength compared to metallic nail systems and no delivery of therapeutic agents.

SUMMARY OF THE INVENTION

The proposed device is an intramedullary nail that functions as both a fracture stabilization device and as a means for delivery of therapeutic and/or diagnostic agents from the intramedullary position to the entire fracture surface. The catheter-based, drug delivery method uniquely provides maximum control over the type, rate and concentration of drug delivered and the ability to deliver the drug to the precise location of bone trauma.

The proposed intramedullary catheter nail is unique in the field of orthopedic surgery. It offers the surgeon a convenient method for obtaining fracture stabilization with the additional benefit of targeted, therapeutic drug delivery. The objects and advantages of the intramedullary catheter nail system are as follows.

1. Stabilization of long bone fractures equivalent to traditional intramedullary nails.
2. Precision delivery of various therapeutic agents from the intramedullary position to the entire fracture surface.
3. Controlled slow dosing of therapeutic agents allowing for constant maintenance of physiologically responsive drug concentrations at the fracture site.

4. Delivery of various drug classes such as growth factors, analgesics, chemotherapeutic, antibiotics, anti-inflammatories, diagnostics or mixtures of various components of differing classes to the fracture site.
5. Unlike bioerodible drug delivery, the intramedullary catheter nail allows for rapid alteration of the drug protocol to better adjust for individual patient responses.
6. Unlike bioerodible drug delivery, the intramedullary catheter nail allows for tailored sequences of drugs to be introduced to the fracture surface.
7. Unlike bioerodible drug delivery, the intramedullary catheter nail allows for periods of no drug delivery such that unassisted bone healing may be observed and evaluated.

DETAILED DESCRIPTION OF THE PREFERRED EMBODIMENTS

Figure 1:
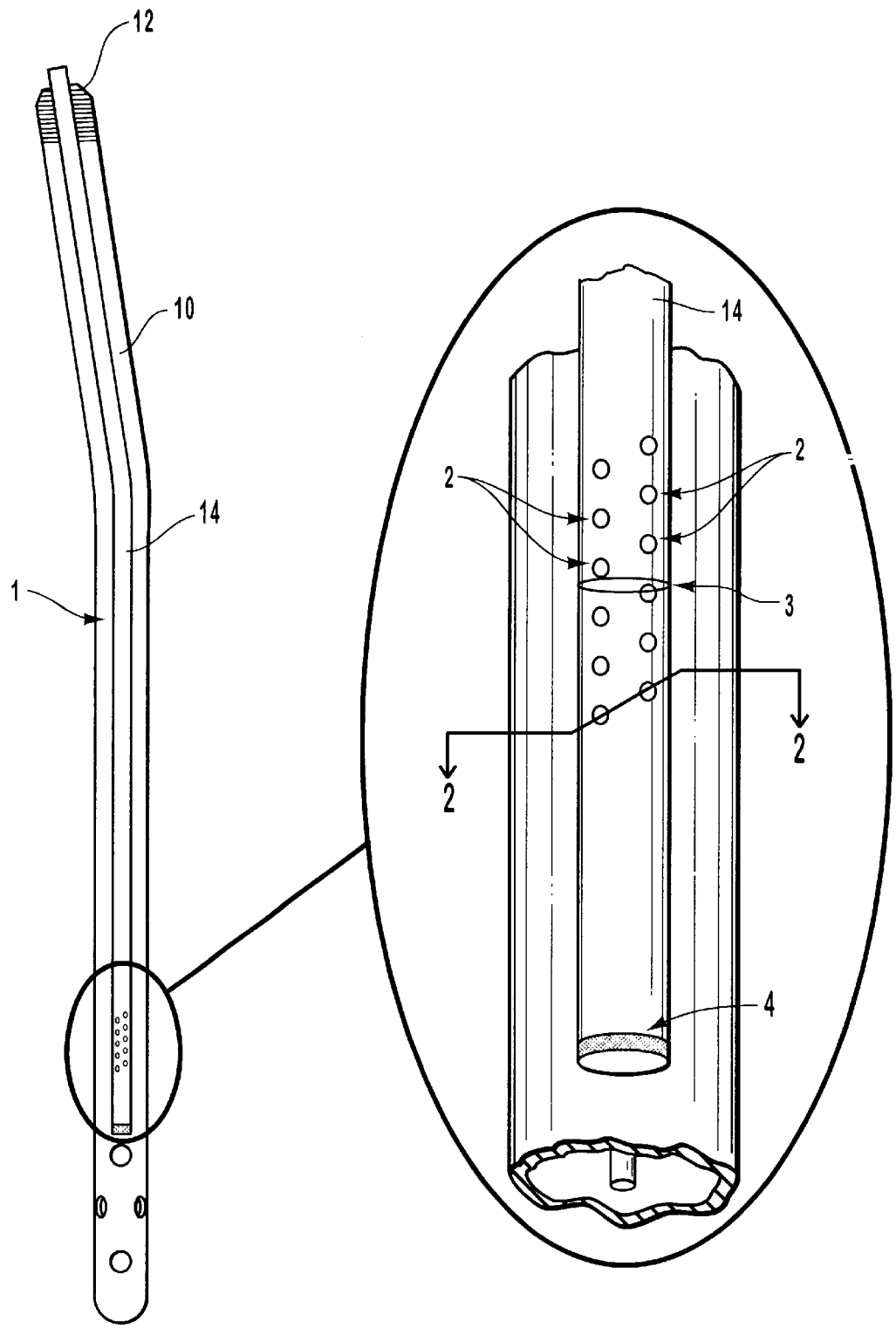
FIG. 1 is a lateral perspective of the intramedullary catheter nail. The end portion of the catheter line is shown in a magnified view adjacent to the view of the entire nail, A preferred embodiment of the intramedullary catheter nail is illustrated.

FIG. 1 is a lateral perspective of the intramedullary catheter nail 10. A catheter line 14 is shown inserted to its maximum depth within the intramedullary nail 10.

Figure 2:
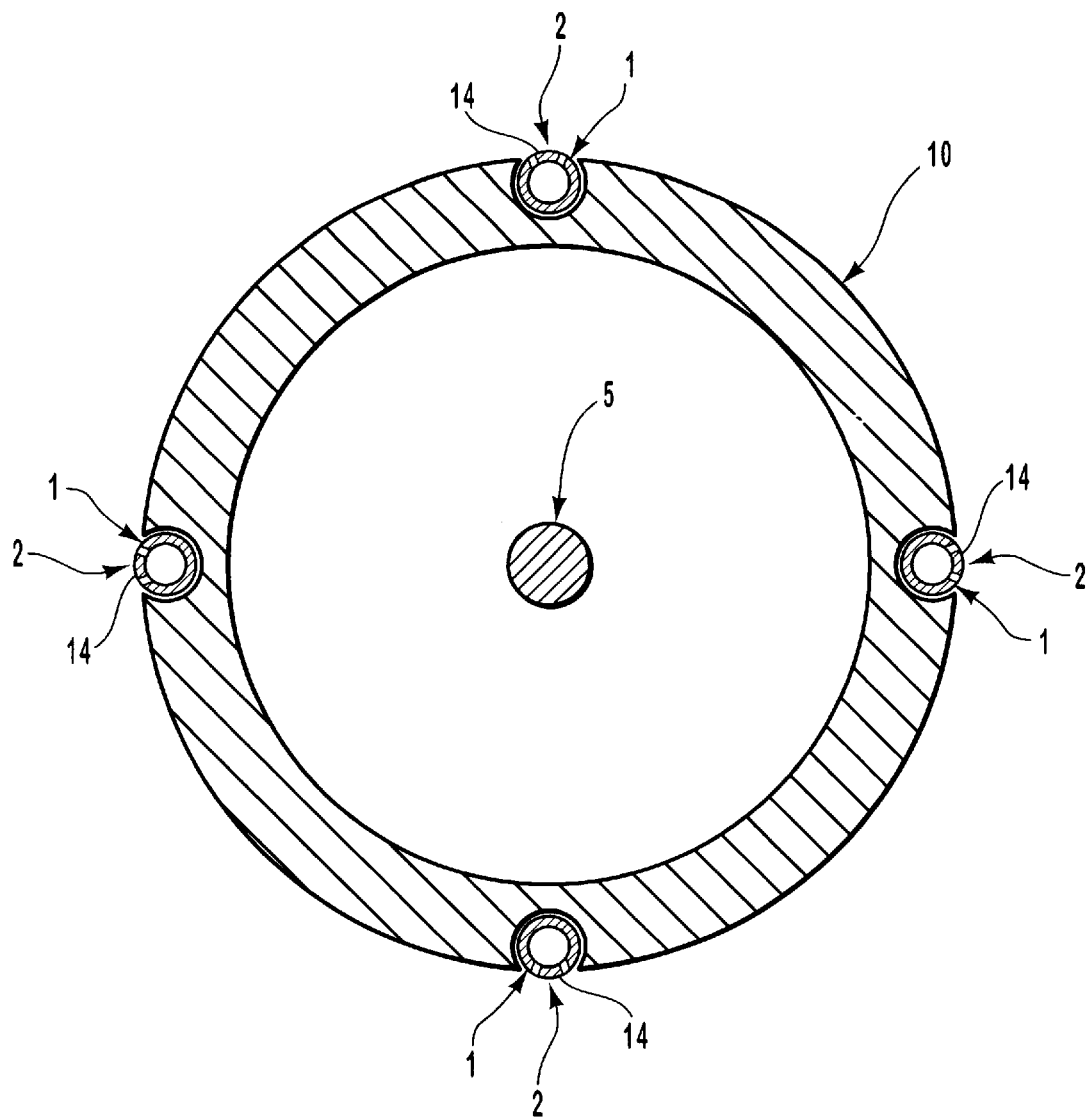
FIG. 2 is a cross-sectional view of the intramedullary catheter nail for the preferred embodiment illustrated in FIG. 1.

FIG. 2 illustrates the means by which the catheter lines 14 are held within the intramedullary nail 10 while allowing for transport of delivered fluid drugs out of the catheter nail 10 and into the surrounding fracture site. Catheter lines 14 are of slightly smaller diameter than the associated channel groove 1 along the length of the intramedullary nail 10. The channel groove 1 is open to the endosteal surface sufficient for elution of delivered agents to the fracture site but constricted enough so as to prevent escape of the catheter lines 14 from the implant device 10. A distance of approximately two inches separates the plugged end 4 of the catheter tube 14 and the beginning of the perforated delivery region 2 of the catheter.

LIST OF REFERENCE NUMERALS
FIG. 1:
1. channel groove
2. perforated region of catheter tube
3. radiographically visible marking ring on catheter tube
4. catheter end plug
10. intramedullary nail
12. proximal end
14. catheter tube FIG. 2 (cross-section of intramedullary nail 10 with catheter tubes 14 located in channel grooves 1):
1. channel grooves
5. insertional guidewire
10. intramedullary nail
14. catheter tubes Description—Main Embodiment
The main embodiment of the intramedullary catheter nail consists of an intramedullary nail 10 of standard dimensions that contains from one to four grooves 1 originating at the proximal end 12 of the nail 10 and running nearly the entire length of the total nail length. The grooves 1 are shaped so as to allow a catheter tube 14 to be positioned within a groove 1 and provide open communication with the adjacent bone (not shown) while still preventing migration of the catheter tube 14 away from the confines of the intramedullary nail 10, particularly the channel groove 1. The catheter tubes 14 utilized in this system are hollow, flexible tubing that is plugged at the catheter end 4 and perforated at multiple points within a perforation zone or region 2 approximately two inches from the imperforate end 4. Centrally located within the perforation zone 2, a radiographically visible ring 3 is embedded within the catheter tube 14.

The materials of construction for the nail portion 10 of the intramedullary catheter nail system are any of the various alloys currently utilized in the field of orthopedic surgery such as but not limited to titanium alloys, cobalt-chrome alloys, stainless steel alloys and polymer composites. The materials of construction for the catheter portion 14 of the intramedullary catheter nail system are any of the various polymer systems currently used for catheter construction such as but not limited to polyethylene, polyurethane, and polyimide. The radiographically visible ring 3 is constructed from highly radio-opaque material such as but not to be limited to the rare earth series of elements such as barium, lanthanum, strontium or yttrium.

Operation—Main Embodiment

The utilization of the intramedullary catheter nail 10 begins with the standard orthopedic procedure of nail insertion and locking screw fixation. The system can be designed for fracture stabilization of any of the long bones of the body. Once fracture stabilization has been obtained, a lateral view radiograph would be taken. The radiographic image is used to verify the alignment of the fracture repair. This image is also used to measure the distance between the present location of the catheter drug delivery perforated zone 2 (radiographically apparent by the marking rings 3) and the fracture site. The distance obtained is set as the distance of catheter retraction so as to position the drug delivery outlet (e.g., the perforated zone 2) as close as possible to the fracture site. After appropriate catheter retraction, a second radiograph may be obtained to verify the location of the catheter drug delivery perforated zone 2 versus the fracture site. If catheter location is adequate, catheter lines 14 are connected to a subcutaneous port (not shown) suitable for injection or connection to a drug pumping device (not shown) such as an infusion pump (not shown). A catheter locking clamp (not shown) may also be employed so as to secure the catheter lines 14 to the implant nail 10 and prevent catheter shifting that may occur due to patient movements. The clamp device (not shown) would be positioned on the end 12 of the intramedullary nail 10 where the catheter lines 14 exit the nail 10. Ideally, the catheter line 14 will be prefilled with sterile, isotonic saline solution so as to minimize the need for purging gas in the catheter line 14. As the therapeutic solution is being pumped to the fracture site, the two inch length of catheter tube 14 that extends beyond the perforated region 2 forces the therapeutic solution into the fracture site openings instead of allowing the solution to run down the remaining unfilled channel groove 1.

Description and Operation—Alternative Embodiments

An alternative embodiment of the intramedullary catheter nail may consist of but not be limited to a nail of standard dimensions that contains one or more internal channels that run along the length of the nail. These channels are positioned such that the thickness of material separating the most radial portion of the channel from the external surface of the nail is thin enough to facilitate mechanical perforation of the outer shell layer. The channels would be structured such that if multiple channels were present, they would join together near their exit point from the nail such that only a single catheter line is needed to supply fluids to all channels.

Prior to nail insertion, the surgeon would extrapolate from radiographic images of the fractured bone what location on the nail will correlate with the fracture site once the nail is thin wall of the nail which covers the channel. Multiple holes may be drilled along each channel and for multiple channels. Once the catheter nail is inserted, catheter lines would be linked to the channel exit port at the nail end and run to a subcutaneous port for access to an external source of therapeutic solutions.

A modification of this design embodiment consists of intramedullary nails with pre-drilled channels along the length of the nail. These holes between the channel space and the outside are plugged with removable polymer stoppers. Sterile polyethylene would be a suitable material for hole plugging. As with the previous embodiment, selection of which stoppers to remove is determined by overlaying the nail on a radiographic image of the long bone to be repaired and correlating the fracture location to the appropriate hole/stopper location.

Another possible design configuration is to fabricate channeled intramedullary nails, as previously detailed, wherein the channels run slightly below the outer surface of the nail. These nails would have pre-drilled perforations into their channel spaces at locations that could be defined as distal, mid-body or proximal. In this manner, a robust inventory of differing nail sizes and perforation locations would allow the surgeon to select the proper catheter intramedullary nail without the drilling, plugger removing or catheter retraction steps of the other embodiments.

The merging of catheter drug delivery and orthopedic devices may be easily extended to produce orthopedic fracture fixation plating systems that elute therapeutic agents at the fracture site.

Conclusion, Ramifications, and Scope

The intramedullary catheter nail is a unique orthopedic device that allows for an advanced level of patient treatment. The intramedullary catheter nail addresses both the mechanical demands of fracture stabilization and the physiological demands of therapeutic drug delivery. With an increasing precentage of the population being of advanced age, the need to stimulate bone growth after traumatic fracture will only increase. A means for efficient delivery of growth factors directly to the fracture site will therefore be a highly utilized tool of significant benefit to the patient population.

Thus, the scope of the invention should be determined by the appended claims and their legal equivalents, rather than by the examples given.

What is claimed is:

1. A bone repair system comprising:
    an intramedullary nail sized and shaped so as to facilitate positioning of said nail within a long bone containing a fractured region in order to strengthen said bone, said nail including a length and a surface;
    at least one channel groove disposed within said intramedullary nail along at least a portion of the length of said intramedullary nail, said channel groove including an opening through the surface of said nail; and
    at least one catheter tube positioned within said at least one channel groove of said intramedullary nail, said catheter tube including a first end for introduction of a medicament therethrough, a second plugged end opposite said first end, and at least one diffusion hole through a surface of said catheter tube through which a medicament may be applied to a desired bone treatment site from said catheter through said opening in said nail, said at least one diffusion hole being positioned relative to said bone treatment site by selective insertion or retraction of said catheter tube relative to said intramedullary nail, wherein said catheter tube seals said channel groove on either side of said at least one diffusion hole so that the medicament flows through said opening in said nail in an area adjacent said at least one diffusion hole rather than along said channel groove.

2. A bone repair system as defined in claim 1, wherein said catheter tube includes a perforated region that includes a plurality of diffusion holes, wherein said catheter tube seals the channel groove on either side of said perforated region so that the medicament flows through said opening in said nail in an area adjacent said perforated region rather than along said channel groove.

3. A bone repair system as defined in claim 2, wherein said perforated region is located approximately two inches from said plugged end of said catheter tube.

4. A bone repair system as defined in claim 1, wherein said catheter tube further includes a radiographically visible marking at or near the diffusion hole that permits radiographic verification of the location of the diffusion hole relative to the fracture site.

5. A bone repair system as defined in claim 4, wherein said radiographically visible marking comprises a radiographically visible ring.

6. A bone repair system as defined in claim 4, wherein said radiographically visible marking comprises a radio-opaque material that includes at least one of barium, lanthanum, strontium, or yttrium.

7. A bone repair system as defined in claim 1, wherein said intramedullary nail includes from between one to four channel grooves, each of which is sized and configured to receive one of said at least one catheter tube.

8. A bone repair system as defined in claim 1, wherein said opening in said channel groove extends through the surface of said nail along an entire length of said channel groove.

9. A bone repair system as defined in claim 1, wherein said intramedullary nail comprises at least one of a titanium alloy, a cobalt-chrome alloy, a stainless steel alloy, or a polymer composite.

10. A bone repair system as defined in claim 1, wherein said catheter tube comprises at least one of polyethylene, polyurethane, or polyimide.

11. A bone repair system comprising:
    an intramedullary nail sized and shaped so as to facilitate positioning of said nail within a long bone containing a fractured region in order to strengthen said bone, said nail including a length and a surface;
    at least one channel groove disposed within said intramedullary nail along at least a portion of the length of said intramedullary nail, said channel groove including an opening through the surface of said nail; and
    at least one catheter tube positioned within said at least one channel groove of said intramedullary nail, said catheter tube including a first end for introduction of a medicament therethrough, a second plugged end opposite said first end, and at least one diffusion hole through a surface of said catheter tube through which a medicament may be applied to a desired bone treatment site from said catheter through said opening in said nail, said at least one diffusion hole being positioned relative to said bone treatment site by selective insertion or retraction of said catheter tube relative to said intramedullary nail, wherein said catheter tube includes at least one radiographically visible marking at or near said at least one diffusion hole.

12. A bone repair system as defined in claim 11, wherein said catheter tube includes a perforated region that includes a plurality of diffusion holes.

13. A bone repair system as defined in claim 12, wherein said radiographically visible marking is centered within the perforated region.

14. A bone repair system as defined in claim 12, wherein said catheter tube seals the channel groove on either side of said perforated region so that the medicament flows through said opening in said nail in an area adjacent said perforated region rather than along said channel groove.

15. A bone repair system, comprising:
 an intramedullary nail sized and shaped so as to facilitate positioning of said nail within a long bone containing a fractured region in order to strengthen said bone, said nail including a length and a surface and at least one channel groove disposed within said intramedullary nail along at least a portion of the length of said intramedullary nail, said channel groove including an opening through the surface of said nail; and
 at least one catheter tube sized and configured for positioning within said at least one channel groove of said intramedullary nail, said catheter tube including a first end for introduction of a medicament therethrough, a second plugged end opposite said first end, and at least one diffusion hole through a surface of said catheter tube through which a medicament may be applied to a desired bone treatment site from said catheter through said opening in said nail, wherein said at least one diffusion hole is positionable relative to said bone treatment site by selectively inserting or retracting said catheter tube relative to said intramedullary nail, wherein said catheter tube is sized relative to said channel groove so as to seal said channel groove on either side of said at least one diffusion hole so that, when the catheter tube is positioned within said channel groove, the medicament flows through said opening in said nail in an area adjacent said at least one diffusion hole rather than along said channel groove.

16. A bone repair system as defined in claim 15, wherein said catheter tube includes a perforated region that includes a plurality of diffusion holes, wherein said catheter tube seals the channel groove on either side of said perforated region so that the medicament flows through said opening in said nail in an area adjacent said perforated region rather than along said channel groove.

17. A bone repair system as defined in claim 16, wherein the perforated region of said catheter tube further includes a radiographically visible marking ring that permits radiographic verification of the location of the perforated region relative to the fracture site.

18. A bone repair system, comprising:
 an intramedullary nail sized and shaped so as to facilitate positioning of said nail within a long bone containing a fractured region in order to strengthen said bone, said nail including a length and a surface and at least one channel groove disposed within said intramedullary nail along at least a portion of the length of said intramedullary nail, said channel groove including an opening through the surface of said nail; and
 at least one catheter tube sized and configured for positioning within said at least one channel groove of said intramedullary nail, said catheter tube including a first end for introduction of a medicament therethrough, a second plugged end opposite said first end, and at least one diffusion hole through a surface of said catheter tube through which a medicament may be applied to a desired bone treatment site from said catheter through said opening in said nail, wherein said at least one diffusion hole is positionable relative to said bone treatment site by selectively inserting or retracting said catheter tube relative to said intramedullary nail, wherein said catheter tube includes at least one radiographically visible marking at or near said at least one diffusion hole.

19. A bone repair system as defined in claim 18, wherein said catheter tube includes a perforated region that includes a plurality of diffusion holes.

20. A bone repair system as defined in claim 19, wherein said catheter tube seals the channel groove on either side of said perforated region so that the medicament flows through said opening in said nail in an area adjacent said perforated region rather than along said channel groove.

* * * * *